(12) United States Patent
Lundquist et al.

(10) Patent No.: US 7,714,303 B2
(45) Date of Patent: May 11, 2010

(54) METHODS AND SYSTEMS FOR ANALYZING FLUORESCENT MATERIALS WITH REDUCED AUTHOFLUORESCENCE

(75) Inventors: Paul Lundquist, San Jose, CA (US); Cheng Frank Zhong, Sunnyvale, CA (US); Denis Zaccarin, San Jose, CA (US); Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 12/151,979

(22) Filed: May 9, 2008

(65) Prior Publication Data

US 2008/0283772 A1    Nov. 20, 2008

Related U.S. Application Data

(60) Provisional application No. 60/928,617, filed on May 10, 2007.

(51) Int. Cl.
 *F21V 9/16* (2006.01)
(52) U.S. Cl. .................................. 250/458.1
(58) Field of Classification Search .............. 250/458.1; 204/603, 612, 452, 461; 501/301
See application file for complete search history.

(56) References Cited

U.S. PATENT DOCUMENTS

| | | | | |
|---|---|---|---|---|
| 5,847,400 | A | * | 12/1998 | Kain et al. ................. 250/458.1 |
| 5,871,628 | A | * | 2/1999 | Dabiri et al. ................. 204/461 |
| 6,613,580 | B1 | | 9/2003 | Chow et al. |
| 6,917,726 | B2 | | 7/2005 | Levene et al. |
| 2004/0017150 | A1 | * | 1/2004 | Fricke et al. ................. 313/501 |
| 2006/0061755 | A1 | | 3/2006 | Turner et al. |
| 2007/0057211 | A1 | | 3/2007 | Bahlman et al. |

FOREIGN PATENT DOCUMENTS

WO    WO 01/01112 A1 *  1/2001

OTHER PUBLICATIONS

Levene et al., "Zero-Mode Waveguides for Single-Molecule Analysis at High Concentrations," 2003, Science, vol. 299, pp. 682-686.*
Yang et al., "Parallel confocal systems for biomedical application," 2001, Proceedings of SPIE, vol. 4378, pp. 127-132.*
Levene et al. (2003) "Zero-mode waveguides for single-molecule analysis at high concentrations" Science 299(5607): 682-686.

* cited by examiner

*Primary Examiner*—David P Porta
*Assistant Examiner*—Kiho Kim
(74) *Attorney, Agent, or Firm*—Robert H. Reamey (57) ABSTRACT

Mitigative and remedial approaches to reduction of autofluorescence background noise are applied in analytical systems that rely upon sensitive measurement of fluorescent signals from arrays of fluorescent signal sources. Such systems are for particular use in fluorescence based sequencing by incorporation systems that rely upon small numbers or individual fluorescent molecules in detecting incorporation of nucleotides in primer extension reactions.

8 Claims, 7 Drawing Sheets

METHODS AND SYSTEMS FOR ANALYZING FLUORESCENT MATERIALS WITH REDUCED AUTOFLUORESCENCE

CROSS-REFERENCE TO RELATED APPLICATIONS

The present application claims priority from Provisional U.S. Patent Application No. 60/928,617, filed May 10, 2007, the full disclosure of which is hereby incorporated by reference in their entirety for all purposes.

STATEMENT AS TO RIGHTS TO INVENTIONS MADE UNDER FEDERALLY SPONSORED RESEARCH AND DEVELOPMENT

Not applicable.

FIELD OF THE INVENTION

The invention is in the field of reducing autofluorescence background noise.

BACKGROUND OF THE INVENTION

Typical fluorescence based optical analysis of analytical reactions employs reactants or other reagents in the reaction of interest that bear a fluorescent moiety, such as a labeling group, where the detection of that moiety is indicative of a particular reaction result or condition. For example, reactions may be engineered to produce a change in the amount, location, spectrum, or other characteristic upon occurrence of a reaction of interest.

During analysis, an excitation light source is directed through an optical system or train at the reaction to excite fluorescence from the fluorescent moiety. The emitted fluorescence is then collected by the optical train and directed toward a detection system, which quantifies, records, and/or processes the signal data from the fluorescence. Fluorescence-based systems are generally desired for their high signal levels deriving from the high quantum efficiency of the available fluorescent dye moieties. Because of these high signal levels, relatively low levels of the materials are generally required in order to observe a fluorescent signal.

Notwithstanding the great benefits of fluorescent reaction systems, the application of these systems does have some drawbacks particularly when used in extremely low signal level reactions, e.g., low concentration or even single molecule detection systems. In particular, these systems often have a number of components that can potentially generate amounts of background signal, e.g., detected signal that does not emanate from the fluorescent species of interest, when illuminated with relatively high intensity radiation. This background signal can contribute to signal noise levels, and potentially overwhelm relatively low reaction derived signals or make more difficult the identification of signal events, e.g., increases, decreases, pulses etc., of fluorescent signal associated with the reactions being observed.

Background signal, or noise, can derive from a number of sources, including, for example, fluorescent signals from non targeted reaction regions, fluorescence from targeted reaction regions but that derive from non-relevant sources, such as non-specific reactions or associations, such as dye or label molecules that have nonspecifically adsorbed to surfaces, prevalence or build up of labeled reaction products, other fluorescent reaction components, contaminants, and the like. Other sources of background signals in fluorescent systems include signal noise that derives from the use of relatively high-intensity excitation radiation in conjunction with sensitive light detection. Such noise sources include those that derive from errant light entering the detection system that may come from inappropriately filtered or blocked excitation radiation, and/or contaminating ambient light sources that may impact the overall system. Other sources of signal noise resulting from the application of high intensity excitation illumination derives from the auto-fluorescence of the various components of the system when subjected to such illumination, as well as Raman scattering of the excitation illumination. The contribution of this systemic fluorescence is generally referred to herein as autofluorescence background noise (ABN).

It would be therefore desirable to provide methods, components and systems in which background signal, such as autofluorescence background noise, was minimized. This is particularly the case in relatively low signal level reactions, such as single molecule fluorescence detection methods and systems. The present invention meets these and other needs.

SUMMARY OF THE INVENTION

The invention provides methods and systems that have improved abilities to monitor fluorescent signals from analytical reactions by virtue of having reduced levels of background signal noise that derives from autofluorescence created within one or more components of the overall system.

In a first aspect, the invention provides systems for monitoring a plurality of discrete fluorescent signals from a substrate. The systems include a substrate onto which a plurality of discrete fluorescent signal sources has been disposed, an excitation illumination source, and a detector for detecting fluorescent signals from the plurality of fluorescent signal sources. In addition, the systems include an optical train positioned to simultaneously direct excitation illumination from the excitation illumination source to each of the plurality of discrete fluorescent signal sources on the substrate and direct fluorescent signals from the plurality of fluorescent signal sources to the detector. The optical train of the systems comprises an objective lens focused in a first focal plane at the substrate for simultaneously collecting fluorescent signals from the plurality of fluorescent signal sources on the substrate, a first focusing lens for receiving the fluorescent signals from the objective lens and focusing the fluorescent signals in a second focal plane, and a confocal filter placed within the second focal plane to filter fluorescent signals from the substrate that are not within the first focal plane.

Optionally, the systems for monitoring a plurality of discrete fluorescent signals from a substrate can include a substrate that comprises first and second opposing surfaces that is positioned such that the first surface of the substrate is more proximal to the optical train than the second surface, and such that the first focal plane is substantially coplanar with the second surface. The systems can optionally include an optical train that simultaneously directs excitation radiation at and collects fluorescent signals from at least 100 discrete fluorescent signal sources, at least 500 discrete fluorescent signal sources, at least 1000 discrete signal sources, or at least 5000 discrete signal sources. The systems can optionally include an optical train that comprises a microlens array and/or a diffractive optical element to simultaneously direct excitation illumination at the plurality of discrete fluorescent signal sources on the substrate.

Each of the plurality of discrete signal sources in the systems described above can optionally comprise a reaction region, e.g., an optically confined region on the substrate, into which a complex comprising a nucleic acid polymerase, a template sequence, and a primer sequence, and at least one fluorescently labeled nucleotide has been disposed. Optionally, the optically confined regions can comprise zero mode waveguides.

The invention also provides second set of systems for monitoring a plurality of discrete fluorescent signals from a substrate, which includes a substrate onto which a plurality of discrete fluorescent signal sources has been disposed, an excitation illumination source, and a detector for detecting fluorescent signals from the plurality of fluorescent signal sources. In addition, the second set of systems of monitoring a plurality of discrete fluorescent signals from a substrate includes an optical train that is positioned to direct excitation illumination from the excitation illumination source to each of the plurality of discrete fluorescent signal sources on the substrate in a targeted illumination pattern. In addition, the optical train directs fluorescent signals from the plurality of fluorescent signal sources to the detector.

Optionally, the optical train in the second set systems for monitoring a plurality of discrete fluorescent signals from a substrate can comprise a microlens array and/or a diffractive optical element to direct excitation radiation to each of the plurality of discrete fluorescent signal sources in a targeted illumination pattern. The diffractive optical element can optionally be configured to direct excitation radiation to at least 100 discrete fluorescent signal sources, at least 500 discrete fluorescent signal sources, at least 1000 discrete fluorescent signal sources, or at least 5000 discrete fluorescent signal sources in a targeted illumination pattern.

In the second set systems for monitoring a plurality of discrete fluorescent signals from a substrate, each of the plurality of discrete signal sources can optionally comprise a reaction region, e.g., an optically confined region on the substrate, into which a complex comprising a nucleic acid polymerase, a template sequence, and a primer sequence, and at least one fluorescently labeled nucleotide has been disposed. The optically confined regions can optionally comprise zero mode waveguides.

In a related aspect, the invention provides methods of reducing fluorescence background signals in detecting fluorescent signals from a substrate that comprises a plurality of fluorescent signal sources. The methods include directing excitation radiation simultaneously at a plurality of fluorescent signal sources on a substrate in a first focal plane, collecting fluorescent signals simultaneously from the plurality of fluorescent signal sources, filtering the fluorescent signals to reduce fluorescence not in the first focal plane to provide filtered fluorescent signals, and detecting the filtered fluorescent signals. The filtering step in the methods can optionally comprise confocally filtering the fluorescent signals to provide filtered fluorescent signals.

The invention also provides methods of detecting fluorescent signals from a plurality of discrete fluorescent signal sources on a substrate. These methods include providing a substrate onto which a plurality of discrete fluorescent signal sources has disposed, directing excitation illumination at the substrate in a targeted illumination pattern, and detecting fluorescent signals from each of the plurality of discrete fluorescent signal sources. The step of directing excitation at the substrate in a targeted illumination pattern can optionally comprise passing the excitation illumination through a microlens array and/or a diffractive optical element. The targeted illumination pattern can optionally comprise at least 100 discrete illumination spots positioned to be incident upon at least 100 discrete fluorescent signal sources, at least 500 discrete illumination spots positioned to be incident upon at least 500 discrete fluorescent signal sources, at least 1000 discrete illumination spots positioned to be incident upon at least 1000 discrete fluorescent signal sources, or at least 5000 discrete illumination spots positioned to be incident upon at least 5000 discrete fluorescent signal sources.

In addition, the invention provides three sets of methods of monitoring fluorescent signals from a source of fluorescent signals. In the first set, the methods include providing a fluorescent signal detection system that comprises a substrate comprising a plurality of discrete fluorescent signal sources, providing a source of excitation illumination, providing a fluorescent signal detector, and providing an optical train for directing excitation illumination from the source of excitation illumination to the substrate and for directing fluorescent signals from the substrate to the fluorescent signal detector. In this set of methods, at least one optical component in the optical train is photobleached so as to reduce a level of autofluorescence produced by the at least one optical component in response to passing excitation illumination therethrough.

The second set of methods of monitoring fluorescent signals from a source of fluorescent signals includes providing a substrate onto which a plurality of discrete fluorescent signal sources have been disposed, directing excitation illumination at the substrate in a targeted illumination pattern to excite fluorescent signals from the fluorescent signal sources, collecting the fluorescent signals from the plurality of discrete fluorescent signal sources illuminated with the targeted illumination pattern, confocally filtering the fluorescent emissions, and separately detecting the fluorescent emissions from the discrete fluorescent signal sources.

The third set of methods of monitoring fluorescent signals from a source of fluorescent signals includes providing an excitation illumination source, providing a substrate onto which at least a first fluorescent signal source has been disposed, and providing an optical train comprising optical components that is positioned to direct excitation illumination from the illumination source to the at least first fluorescent signal source and for transmitting fluorescent signals from the at least first fluorescent signal source to a detector. The third set of methods includes photobleaching at least one of the optical components to reduce an amount of autofluorescence produced by the at least one optical component in response to the excitation illumination, directing excitation illumination through the at least one optical component and at the at least first fluorescent signal source, and detecting fluorescent signals from the at least first fluorescent signal source. In the third set of methods, the fluorescent signals can optionally be confocally filtered prior to being detected.

Relatedly, the invention provides systems for detecting fluorescent signals from a plurality of signal sources on a substrate. These systems include a source of excitation illumination, a detection system, and an optical train positioned to direct excitation illumination from the source of excitation illumination to the plurality of signal sources on the substrate and transmit emitted fluorescence from the plurality of fluorescent signal sources to the detector. The optical train in these systems includes an objective lens that has a ratio of excitation illumination to autofluorescence of greater than $1 \times 10^{-10}$.

Those of skill in the art will appreciate that that the methods provided by the invention, e.g., for detecting a plurality of discrete fluorescent signals from a plurality of discrete locations on a substrate, for reducing fluorescence background signals in detecting fluorescent signals from a substrate that comprises a plurality of fluorescent signal sources, and/or for monitoring fluorescent signals from a source of fluorescent signals, can be used alone or in combination and can be used in combination with any one or more of the systems described herein. In addition to the foregoing, the invention is also directed to the use of any of the foregoing systems and/or methods in a variety of analytical operations.

DETAILED DESCRIPTION OF THE INVENTION

I. General Discussion of Invention

The present invention generally provides methods, processes and systems for monitoring fluorescent signals associated with reactions of interest, but in which background signal levels and particularly autofluorescence background noise of system components, is reduced.

The methods, processes and systems of the invention are particularly suited to the detection of fluorescent signals from signal sources, e.g., reaction regions, on substantially planar substrates, and particularly for detection of relatively low levels of fluorescent signals from such reaction regions, where signal background has a greater potential for negative impact.

For ease of discussion, the present invention is described in terms of its application to arrays of single molecule reaction regions on planar substrates from which fluorescent signals emanate, which signals are indicative of a particular reaction occurring within such reaction regions. Though described in terms of such single molecule arrays, it will be appreciated that the invention, as a whole, or in part, will have broader applicability and may be employed in a number of different applications, such as in detection of fluorescent signals from other array formats, e.g., spotted arrays, arrays of fluidic channels, conduits or the like, or detection of fluorescent signals from multiwell plate formats, fluorescent bar-coding techniques, and the like.

One exemplary analytical system or process in which the invention is applied is in a single molecule DNA sequencing operation in which an immobilized complex of DNA polymerase, DNA template and primer are monitored to detect incorporation of nucleotides or nucleotide analogs that bear fluorescent detectable groups. See, e.g., U.S. Pat. Nos. 7,033,764, 7,052,847, 7,056,661, and 7,056,676, the disclosures of which are incorporated herein by reference in their entirety for all purposes. Typically, large numbers of complexes are provided immobilized upon transparent substrates, e.g., glass, quartz, fused silica, or the like, and positioned such that individual complexes are optically resolvable when associated with a fluorescent labeling group or molecule, such as a labeled nucleotide or nucleotide analog.

In preferred aspects, the individual complexes may be provided within an optically confined space, such as a zero mode waveguide, where the substrate comprises an array of zero mode waveguides housing individual complexes. In this aspect, an excitation light source is directed through a transparent substrate at an immobilized complex within a zero mode waveguide core. Due to the cross-sectional dimension of the waveguide core in the nanometer range, e.g., from about 20 to about 200 nm, the excitation light is unable to propagate through the core, and evanescent decay of the excitation light results in an illumination volume that only extends a very short distance into the core. As such, an illumination volume that contains one or a few complexes results. Zero mode waveguides and their application in sequencing and other analyses are described in, e.g., U.S. Pat. Nos. 6,917,726, 7,013,054, and 7,181,122, the full disclosures of which are incorporated herein by reference in their entirety for all purposes.

Other approaches to optical confinement may also be employed. For example, total internal reflectance fluorescence microscopy may be used to confine the illumination to near the surface of a substrate. This provides a similar confining effect as the zero mode waveguide, but does so without providing a structural confinement as well. Still other optical confinement techniques may generally be applied, such as those described in U.S. Pat. Nos. 7,033,764, 7,052,847, 7,056,661, and 7,056,676, previously incorporated herein by reference.

In order to optimize the throughput of the sequencing process, multiple different reactions represented in multiple waveguide cores in individual arrays are illuminated and observed simultaneously.

Figure 1:
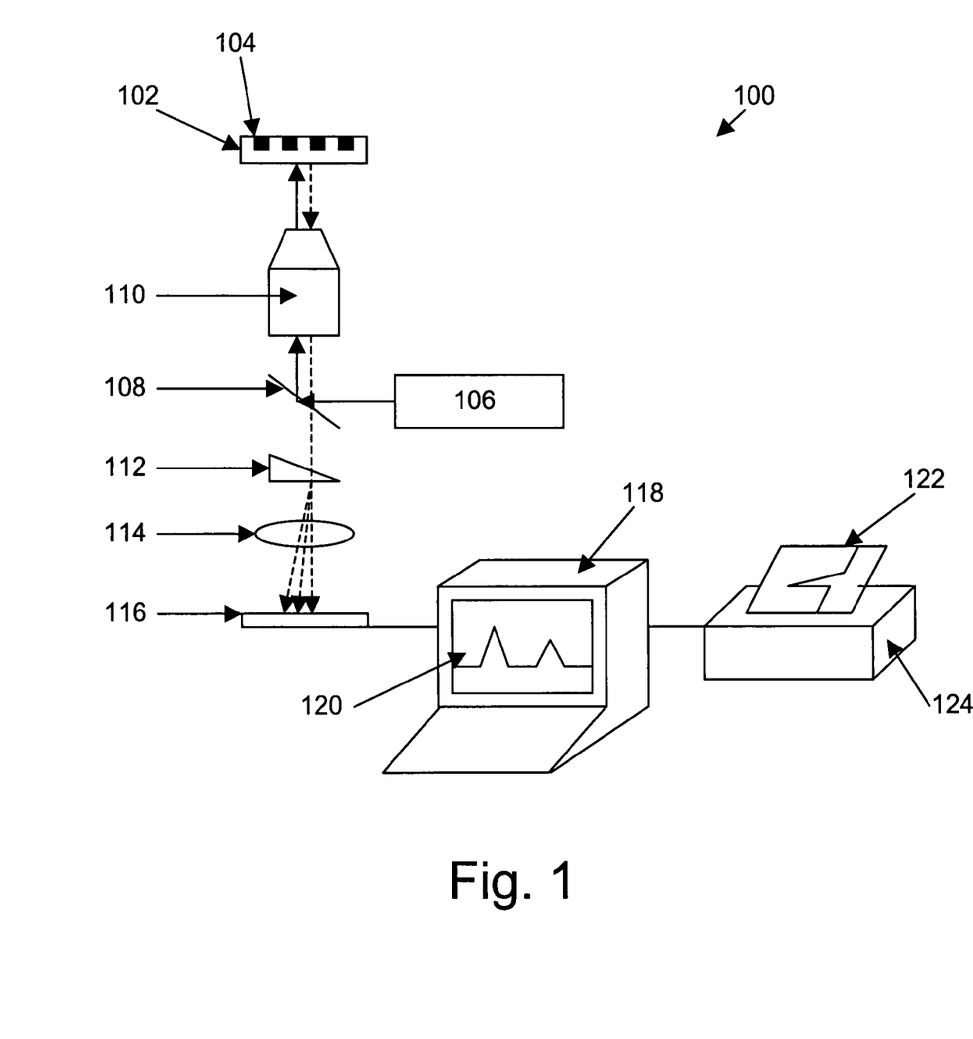
FIG. 1 provides a schematic overview of a fluorescence detection system.

The above described arrays are typically interrogated using a fluorescence detection system that directs excitation radiation at the various reaction regions in the array and collects and records the fluorescent signals emitted from those regions. A simplified schematic illustration of these systems is shown in FIG. 1. As shown, the system 100 includes a substrate 102 that includes a plurality of discrete sources of fluorescent signals, e.g., an array of zero mode waveguides 104. An excitation illumination source, e.g., laser 106, is provided in the system and is positioned to direct excitation radiation at the various fluorescent signal sources. This is typically done by directing excitation radiation at or through appropriate optical components, e.g., dichroic 108 and objective lens 110, that direct the excitation radiation at the substrate 102, and particularly the signal sources 104. Emitted fluorescent signals from the sources 104 are then collected by the optical components, e.g., objective 110, and passed through additional optical elements, e.g., dichroic 108, prism 112 and lens 114, until they are directed to and impinge upon an optical detection system, e.g., detector array 116. The signals are then detected by detector array 116, and the data from that detection is transmitted to an appropriate data processing unit, e.g., computer 118, where the data is subjected to interpretation, analysis, and ultimately presented in a user ready format, e.g., on display 120, or printout 122, from printer 124.

With respect to the exemplary sequencing systems described above, sources of autofluorescence background noise can typically include the components of the optical train through which the excitation radiation is directed, including the objective lens 110 or lenses, the dichroic filter(s) 108, and any other optical components, i.e., filters, lenses, etc., through which the excitation radiation passes. Also contributing to this autofluorescence background noise are components of the substrate upon which the monitored sequencing reactions are occurring, which, in the case of zero mode waveguide arrays for example, include the underlying transparent substrate that is typically comprised of glass, quartz or fused silica, as well as the cladding layer that is disposed upon the substrate, typically a metal layer such as aluminum.

In general, the present invention provides both preventive and remedial approaches to reducing impacts of autofluorescence background noise, in the context of analyses that employ illuminated reactions. Restated, in a first general preventive aspect, the invention is directed to processes and systems that have a reduced level of autofluorescence background noise that is created and that might be ultimately detected by the system. In the additional or alternative remedial aspects, the invention provides methods and systems in which any autofluorescence background noise that is created, is filtered, blocked or masked substantially or in part from detection by the system. As will be appreciated, in many cases, both preventative and remedial approaches may be used in combination to reduce autofluorescence background noise.

II. Preventive Measures

In a first aspect, the present invention reduces the level of autofluorescence background noise generation by preventing or reducing the production of that background noise in the first instance. In particular, this aspect of the invention is directed to providing illumination of the optical signal source or sources in a way that reduces or minimizes the generation of such autofluorescence background noise.

In accordance with one aspect of the invention, the reduction in autofluorescence creation is accomplished by reducing the amount of illumination input into the system and/or directed at the substrate, e.g., by providing highly targeted illumination of only the locations that are desired to be illuminated, and preventing illumination elsewhere in the array or system. By using highly targeted illumination, one simultaneously reduces the area of the substrate that might give rise to autofluorescence, and reduces the overall amount of input illumination radiation required to be input into the system, as such input illumination is more efficiently applied.

In particular, the amount of illumination power required to be applied to the system increases with the number of signal sources that are required to be illuminated. For example, in a zero mode waveguide array that is configured in a gridded format of rows and/or columns of waveguides, multiple waveguides are generally illuminated using a linear illumination format (See, e.g., International Patent Application Nos. US2007/003570 and US2007/003804, which are incorporated herein by reference in their entirety for all purposes). Multiple rows and/or columns are then illuminated with multiple illumination lines.

Figure 2:
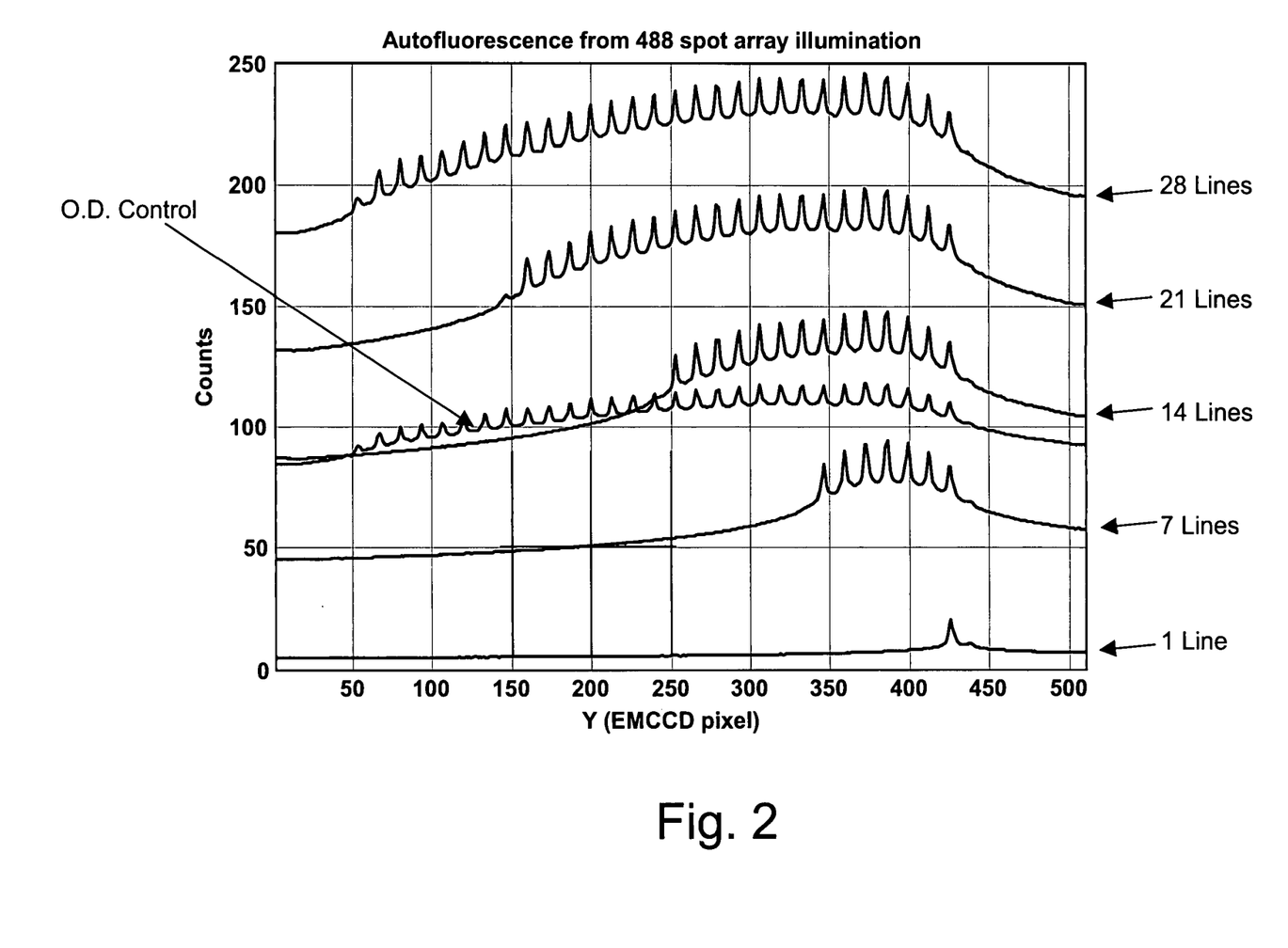
FIG. 2 shows a plot of fluorescent signals as a function of the number of illumination lines applied to a given fluorescently spotted substrate, showing increasing background fluorescence levels with increasing illumination.

As shown in FIG. 2, as the number of illumination lines increases, it results in a linear increase in the amount of autofluorescence emanating from the system. In particular, FIG. 2 shows a plot of fluorescent signals emanating from a spotted array of Alexa488 fluorescent dye spots on a fused silica slide. As can be seen, as more illumination lines are applied to the array, the baseline fluorescence level attributable to autofluorescence background noise increases linearly with the number of illumination lines. Further, it has been demonstrated that this autofluorescence background noise derives not only from the substrate, but also from the other optical components of the system, such as the objective lens and dichroic filter(s).

Accordingly, in a first aspect, the invention reduces the amount of autofluorescence background noise by reducing the amount of excitation illumination put into the system, while still producing the desired fluorescent signals. In general, providing the same or similar levels of excitation illumination at desired locations, e.g., on the substrate, while reducing overall applied excitation illumination in the system, is accomplished through more efficient use of applied illumination by targeting that illumination only to the desired locations. In particular, by targeting illumination only at the relevant locations, e.g., primarily at only the waveguides on an array, one can reduce the amount of power required to be directed into the system to accomplish the desired level of illumination and at the substrate, yielding a consequent reduction in the amount of autofluorescence background noise that is generated at either of the substrate or those optical components through which such illumination power is directed. Additionally, because less of the substrate is being illuminated by virtue of the targeted nature of the illumination, less of the substrate will be capable of contributing to the autofluorescence background noise.

Figure 3A:
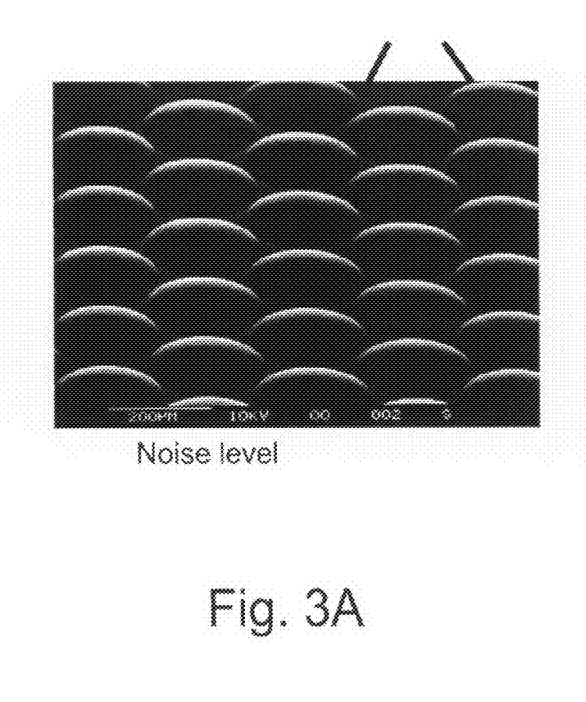
FIG. 3 provides an example of a microlens array for use in the present invention.
Figure 3B:
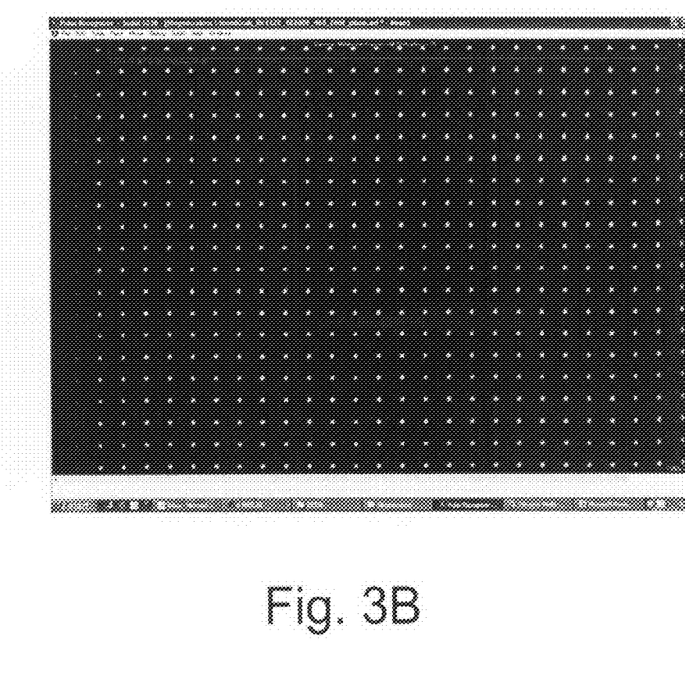

Targeting illumination to each of an array of point targets such as zero mode waveguides, can be accomplished by a number of methods. For example, in a first aspect, excitation radiation may be directed through a microlens array in conjunction with the objective lens, in order to generate spot illumination for each of a number of array locations. In particular, a lens array can be used that would generate a gridded array of illumination spots that would be focused upon a gridded array of signal sources, such as zero mode waveguides, on a substrate. An example of a microlens array is shown in FIG. 3, panel A. In particular, shown is an SEM image of the array. Panel B of FIG. 3 illustrates the illumination pattern from the microlens array used in conjunction with the objective lens of the system. As will be appreciated, the lens array is fabricated so as to be able to focus illumination spots on the same pitch and position as the locations on the array that are desired to be illuminated.

In an alternative aspect, a plurality of illumination spots for targeted illumination of signal sources may be generated by passing excitation illumination through one or more diffractive optical elements ("DOE") upstream of the objective lens. In particular, DOEs can be fabricated to provide complex illumination patterns, including arrays of large numbers of illumination spots that can, in turn, be focused upon large numbers of discrete targets.

Figure 4A:
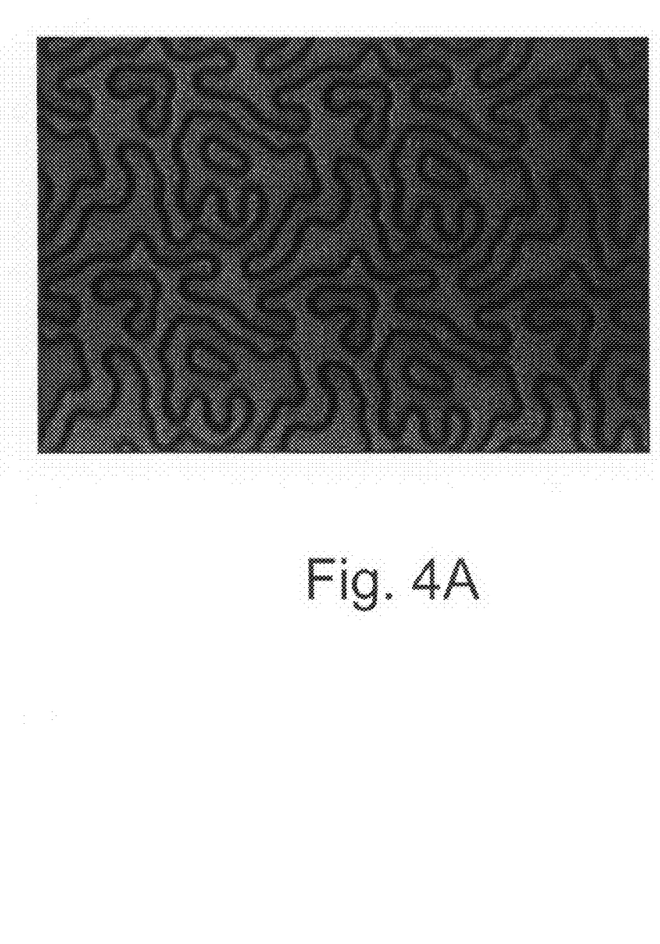
FIG. 4 shows an image of diffractive optical element ("DOE") and the illumination pattern generated when light is passed through the DOE.
Figure 4B:
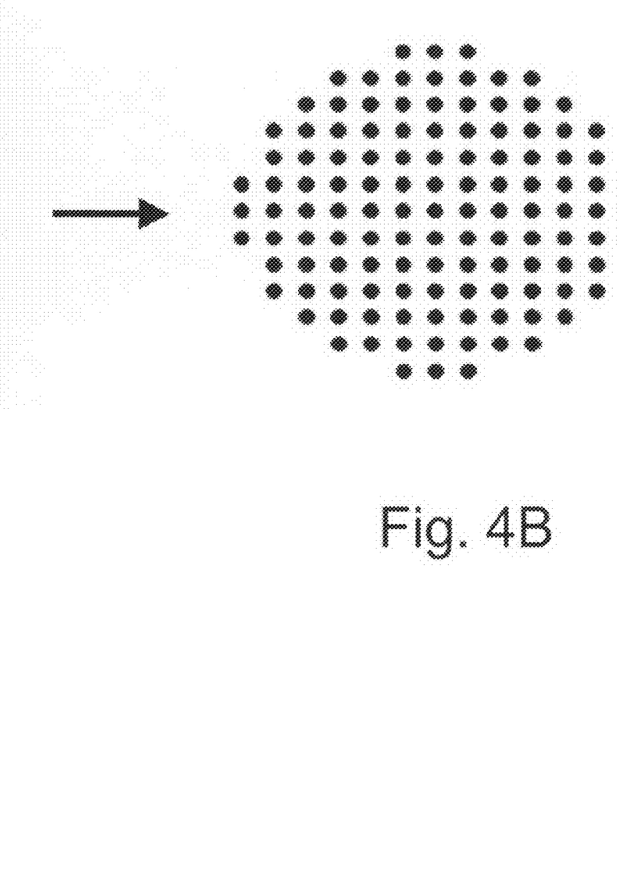

For example, as shown in FIG. 4, a DOE Phase mask, as shown in Panel A, can generate a highly targeted illumination pattern, such as that shown in panel B, which provides targeted illumination of relatively large numbers of discrete locations on a substrate, simultaneously. In particular, the DOE equipped optical system can generally separately illuminate at least 100 discrete signal sources, e.g., zero mode waveguides, simultaneously and in a targeted illumination pattern. In preferred aspects, the DOE may be used to simultaneously illuminate at least 500 discrete signal sources, and in more preferred aspects, illuminate at least 1000, at least 5000, or at least 10,000 or more discrete signal sources simultaneously, and in a targeted illumination pattern, e.g., without substantially illuminating other portions of a substrate such as the space between adjacent signal sources preferably between adjacent illumination spots.

Several approaches can be used to design and fabricate a DOE for use in the present invention. The purpose here is to evenly divide the single laser beam into a large number of discrete new beams, e.g., up to 5000 or more new beams, each with 1/5000 of the energy of the original beam, and each of the 5000 "beamlets" traveling in a different direction. By way of example, the DOE design requirement is to evenly space the beamlets in angles (the 2 angles are referred to herein as $\theta_x$ and $\theta_y$). By analogy, if one provides a diffraction grating that provides equal amplitude to the different orders, and illuminates it with a laser beam, it will result in a row of illuminated dots, corresponding to discrete beams each traveling at a unique angle after they impinge on the grating. If a second similar grating is placed adjacent to the first but rotated by 90 degrees, it will provide a 2 dimensional grid of beamlets, each traveling with a unique $\theta_x$ and $\theta_y$. If the 2 gratings are identical, a square grid will result, but if the 2 gratings have different period, a rectangular grid will result.

As will be appreciated, the DOE (and the Microlens Array) will divide the light into numerous beams that are propagating at unique angles. In a preferred illumination scheme the DOE is combined with the objective lens in a planned way, such that the objective lens will perform a fourier transform on all of the beamlets. In this fourier transform, angle information is converted into special information at the image plane of the objective. After the beamlets pass through the objective, each unique $\theta_x$ and $\theta_y$ will correspond to a unique x,y location in the image plane of the objective. The objective properties must be known in order to correctly design the DOE or microlens. The formula for the fourier transform is given by:

$$(x,y) = EFL \times Tangent(\theta_x, \theta_y),$$

where EFL is the Effective Focal Length of the objective.

There are several different approaches to producing a DOE that will meet the needs of the invention. For example, one approach is through the use of a phase mask that is pixelated such that each pixel will retard the incident photons by a programmed amount. This phase retardation can again be achieved in different ways. For example, one preferred approach uses thickness of the glass element. For example, the phase mask might include a ½ inch square piece of $SiO_2$. Material is etched away from the top surface of the $SiO_2$ plate to, e.g., 64 different etch depths. This is referred to as a 64-level grey scale pattern. The final phase mask then is comprised of a pixelated grid where each pixel is etched to a particular depth. The range of etch depths corresponds to a full $2\pi$ of phase difference. Restated, a photon which impinges on a pixel with the minimum etch depth (no etching) will experience exactly $2\pi$ additional phase evolution compared to a photon which strikes a maximum etch depth (thinnest part of the $SiO_2$). The pixelated pattern etched into the DOE is repeated periodically, with the result that the lateral position of the laser beam impinging on the mask is unimportant.

As will be appreciated, the actual phase evolution for the DOE is a function of the optical wavelength of the light being transmitted through it, so DOE devices will generally be provided for a specific wavelength of excitation illumination.

By targeted illumination or targeted illumination pattern, in accordance with the foregoing, is meant that the illumination directed at the substrate is primarily incident upon the desired locations, rather than other portions of the substrate. For example, as alluded to above, where one desires to interrogate a number of discrete locations on a substrate for fluorescent signals, using targeted illumination would include directing discrete illumination spots at each of a plurality of the different discrete locations. Such targeted illumination is in contrast to illumination patterns that illuminate multiple locations with a single illumination spot or line, in flood or linear illumination profiles. Again, as noted above, targeting illumination provides the cumulative benefits of reducing the required amount of illumination input into the system, and illuminating less area of the substrate, both of which contribute to the problem of autofluorescence background noise.

In particular, targeted illumination, as used herein, can be defined from a number of approaches. For example, in a first aspect, a targeted illumination pattern refers to a pattern of illuminating a plurality of discrete signal sources, reaction regions or the like, with a plurality of discrete illumination spots. While such targeted illumination may include ratios of illumination spots to discrete signal sources that are less than 1, i.e., 0.1, 0.25, or 0.5 (corresponding to one illumination spot for 10 signal sources, 4 signal sources and 2 signal sources, respectively) in particularly preferred aspects, the ratio will be 1 (e.g., one spot for one signal source, i.e., a waveguide).

Alternatively, as a goal of targeted illumination in the context of the present invention is to reduce autofluorescence from excessive illumination, targeted illumination denotes illumination where a substantial percentage of the illumination that is incident upon the substrate is incident upon the desired signal source(s) as opposed to being incident on other portions of the substrate. Accounting for the often small size of signal sources, e.g., in the case of nanoscale zero mode waveguides, as well as the tolerance in direction of illumination by optical systems, such targeted illumination will typically result in at least 5% of the illumination incident upon the overall substrate being incident upon the discrete signal sources themselves. This corresponds to 95% or less wasted illumination that is incident elsewhere. In preferred aspects, that percentage is improved such at least 10%, 20% or in highly targeted illumination patterns, at least 50% of the illumination incident upon the substrate is incident upon the discrete signal sources. Conversely, the amount of illumination incident upon other portions of the substrate is less than 90%, less than 80% or in highly targeted aspects, less than 50%. Determination of this percentage is typically a routine matter of dividing the area of a substrate that is occupied by the relevant signal discrete source divided by the area of total illumination, multiplied by 100, where a region is deemed "illuminated" for purposes of this determination if it exceeds a threshold level of detectable illumination from the illumination source, e.g., 5% of that at the maximum point of a given illumination spot of the same substrate.

In still a further aspect, targeted illumination may be identified through the amount of laser power required to illuminate discrete signal sources vs. illuminating such signal sources using a single flooding illumination profile, e.g., that simultaneously illuminates an entire area in which the plurality of discrete sources is located, as well as the space between such sources. Preferably, the efficiency in targeted illumination over such flood illumination will result in the use of 20% less laser power, preferably 30% less laser power, more preferably more than 50% less laser power, and in some cases more than 75%, 90% or even 99% less laser power to achieve the same illumination intensity at the desired locations, e.g., the signal sources. As will be appreciated, the smaller the discrete illumination spot size, e.g., the more targeted the illumination, the greater the susceptibility of the system to alignment and drift issues, and calibration efforts will need to be increased.

In addition to the advantages of reduced autofluorescence, as set forth above, targeted illumination also provides benefits in terms of reduced laser power input into the system which consequently reduces the level of laser induced heating of reaction regions.

Figure 6:
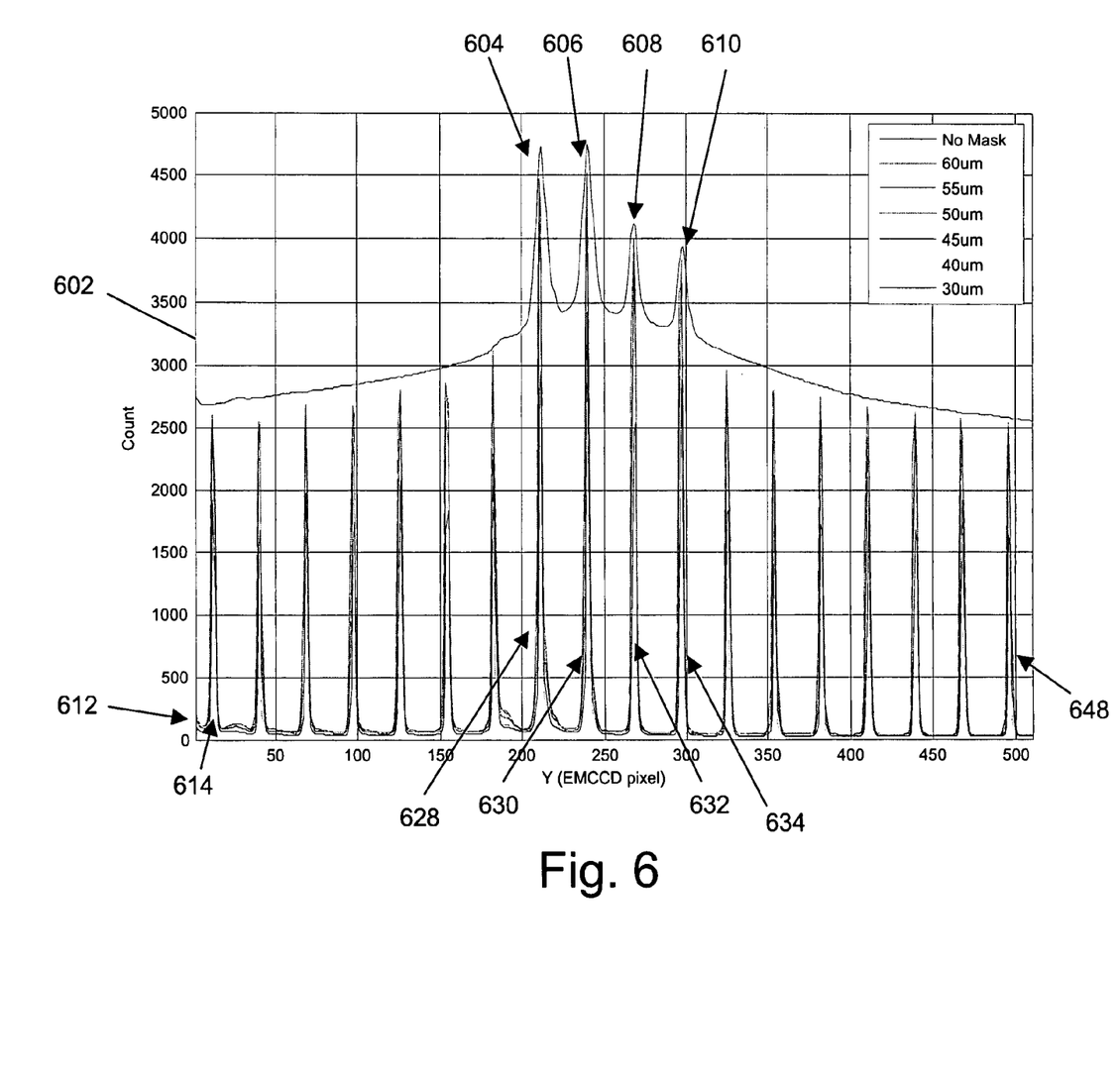
FIG. 6 shows a comparison plot of autofluorescence of a fluorescent detection system in the absence and presence of a confocal mask in the system, to filter out of focus autofluorescence components.

In another preventive approach, an overall optical system or one or more components through which the excitation illumination passes, may be treated to reduce the amount of autofluorescence background noise generated by the system components. By way of example, in an overall optical system, e.g., as schematically illustrated in FIG. 1, illumination may be applied to the system that results in a photobleaching of some or all of the elements of the various components that are fluorescing under normal illumination conditions. Typically, this will require an elevated illumination level relative to the normal analytical illumination conditions of the system. Photobleaching of the optical components may be carried out by exposing the optical train to illumination that is greater in one or both of intensity or power and duration. Either or both of these parameters may be from 2×, 5×10× or even greater than that employed under conventional analysis conditions. For example, exposure of the optical train to the excitation illumination for a prolonged period, e.g., greater than 10 minutes, preferably greater than 20 minutes, more preferably greater than 50 minutes, and in some cases greater than 200 or even 500 minutes, can yield substantial decreases in autofluorescence background noise emanating from the system components. In one particular exemplary application, a 20 mW, 488 nm laser can be used to illuminate the overall system for upwards of 20 hours in order to significantly reduce autofluorescence from the components of such system. FIG. 6 shows a plot of autofluorescence counts in a system illuminated with a 20 mW 488 nm laser, following exposure of the optical train to 'burn in' illumination from a 7.5 mW laser at 488 nm from 0 to 1000 minutes, followed by illumination from a 162 mW laser at 488 nm from 1000 to 4600 minutes. Alternatively or additionally, other illumination sources may be employed to photobleach the optical components, including, e.g., lasers of differing wavelengths, mercury lamps, or the like. As will be appreciated, the photobleaching of the optical components may be carried out at a targeted illumination profile, e.g., a relatively narrow wavelength range such as 488 nm laser illumination, or it may be carried out under a broader spectrum illumination, depending upon the nature of the components to be photobleached and the underlying cause of the autofluorescence.

In other preventive approaches to autofluorescence mitigation, the present invention also utilizes optical elements in the optical train or the overall system that are less susceptible to generating autofluorescence background noise. In particular, it has been determined that a substantial amount of autofluorescence from more complex optical systems derives from coatings applied to the optical components of the system, such as the coatings applied to dichroic filters and objective lenses. As a result, it will be appreciated that additional gains in the reduction of autofluorescence can be obtained through the selection of appropriate optical components, e.g., that have reduced autofluorescence. For example, in selecting an objective lens, it will typically be desirable to utilize an objective that provides a reasonably low ratio of autofluorescence to illumination, as determined on a photon count ratio. For example, in the case of a variety of objective lenses, this ratio has been determined at, e.g., $1.5 \times 10^{-10}$ and $3.2 \times 10^{-10}$ for Olympus model objective lenses UIS2Fluorite 60× Air objective and 40× Air Objective, respectively. Conversely, objectives that have been selected or treated to have reduced autofluorescence will typically have a ratio that is greater than this, e.g., greater than $1 \times 10^{-10}$. By way of example, an Olympus model UIS1 APO 60× Air Objective provided a ratio of $6 \times 10^{-11}$ following a photobleaching exposure as described above.

As noted above, selection of components to fall within the desired levels of autofluorescence will in many cases select for components that have fewer or no applied coating layers, or that have coating layers that are selected to have lower autofluorescence characteristics under the particular applied illumination conditions. Of particular relevance to the instant aspect is the selection of dichroic filters that have been selected to have lower autofluorescence deriving from their coatings, either through selection of coating materials or use of thinner coating layers.

III. Prevention of Detection of Autofluorescence

In an alternative or additional aspect, the invention is directed to a remedial approach to background signal levels, e.g., that reduce the amount of background signal or autofluorescence that is detected or detectable by the system. Typically, this aspect of the invention is directed to filtering signals that are derived from the signal sources or arrays in such a way that highly relevant signals, e.g., those from the signal sources and not from irrelevant regions, are detected by the system. As will be appreciated, this aspect of the invention may be applied alone, or in combination with the preventive measures set forth above, in order to maximize the reduction of the impact of background signal levels.

In the context of one aspect of the invention, it has been determined that a large amount of the autofluorescence background noise constitutes "out of focus" fluorescence, or fluorescence that is not within the focal plane of the system when analyzing a given reaction region or regions. For example, autofluorescence that derives from the substrate portion of the overall systems of the invention, e.g., substrate 102 in FIG. 1, derives from locations in the substrate that are outside of the focal plane of the optical system. In particular, where the optical system is focused upon the back surface of the substrate, the autofluorescence that derives from the entirety of the thickness of the substrate, from the cladding layer above the back surface of the substrate, or from other points not within the focal plane of the system, will generally be out of focus. Likewise, autofluorescence from optical components of the system that are subjected to excitation illumination also are typically not within the focal plane of the instrument. Such components include, for example and with reference to FIG. 1, objective lens 110, and dichroic 108. Because these components transmit the full excitation illumination, they are more prone to emitting autofluorescence. However, the majority of this autofluorescence will be out of the focal plane of the system.

Figure 5:
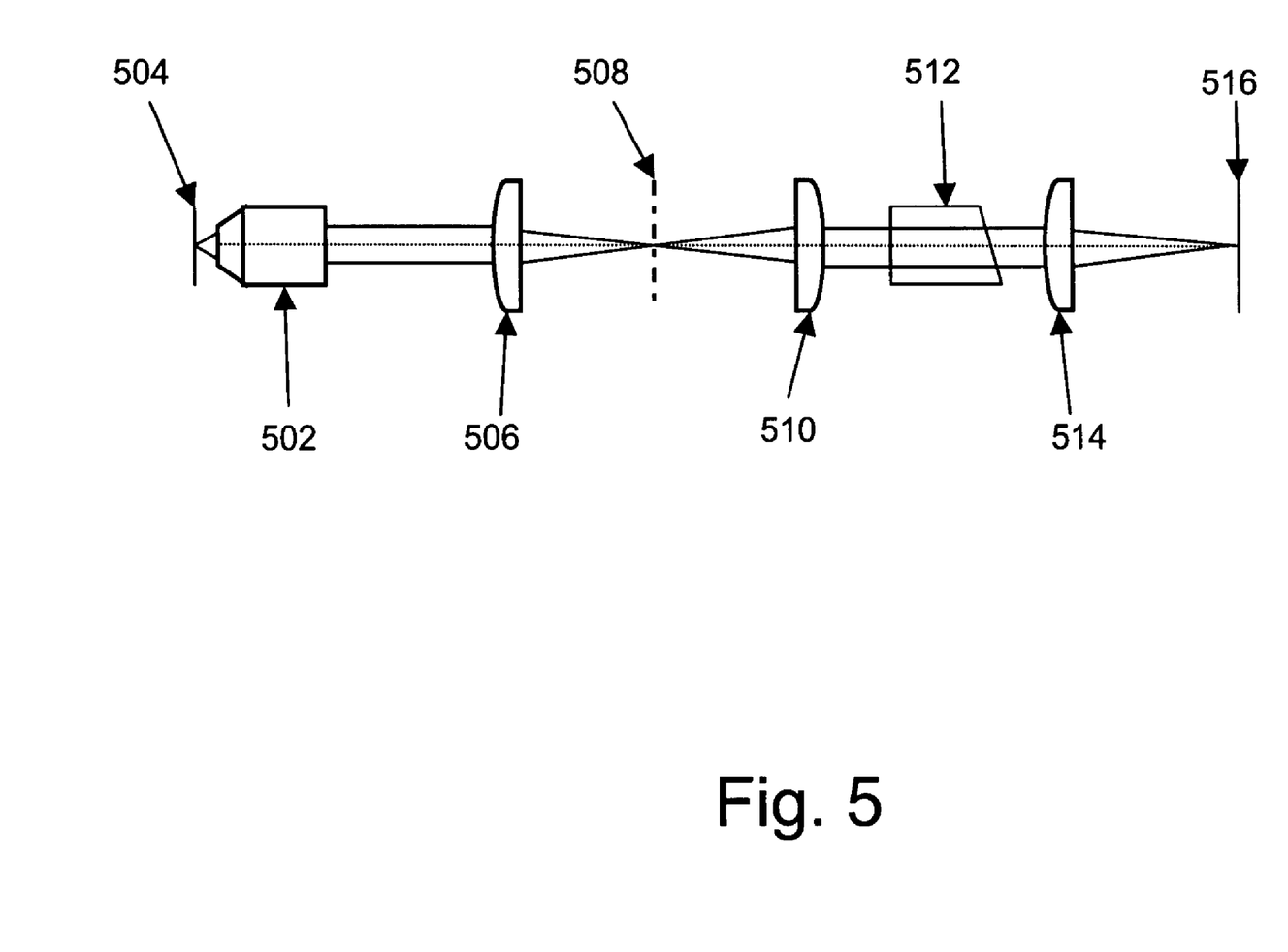
FIG. 5 provides a schematic of an optical train incorporating a confocal mask.

Accordingly, in at least one aspect, the invention employs a spatial filter component to filter out autofluorescence that is out of the focal plane of the objective lens. One example of such a spatial filter includes a confocal mask or filter placed in the optical train. An example of an optical train including such a confocal filter is schematically illustrated in FIG. 5. As shown, an objective lens 502 is positioned adjacent to a substrate, such as zero mode waveguide array 504 having the reaction regions of interest disposed upon it, so as to collect signals emanating from the substrate, as well as any autofluorescence that emanates from the substrate. The collected fluorescence is then focused through a first focusing lens 506. A confocal mask 508 is placed in the focal plane of the first focusing lens 506. Spatially filtered fluorescence that is passed by the confocal mask is then refocused through a second focusing lens 510 and passed through the remainder of the optical train. As shown, this includes a wedge prism 512 to spatially separate spectral components of the fluorescence, and third focusing lens 514, that focuses the image of the fluorescence derived from the focal plane of the objective 502, onto a detector, such as EMCCD 516. By placing the confocal mask in the focal plane of the first focusing lens 506, autofluorescence components that are out of the focal plane of the objective lens (and thus not focused by the focusing lens at the confocal mask 508) will be blocked or filtered, and only fluorescence that is in the focal plane, e.g., fluorescent signals and any autofluorescence that exists in the focal plane, will be passed and imaged upon the detector 516, and detected. In comparative experiments, autofluorescence background signals were reduced approximately 3 fold through the incorporation of a confocal mask, in both two and three laser systems.

Figure 7:
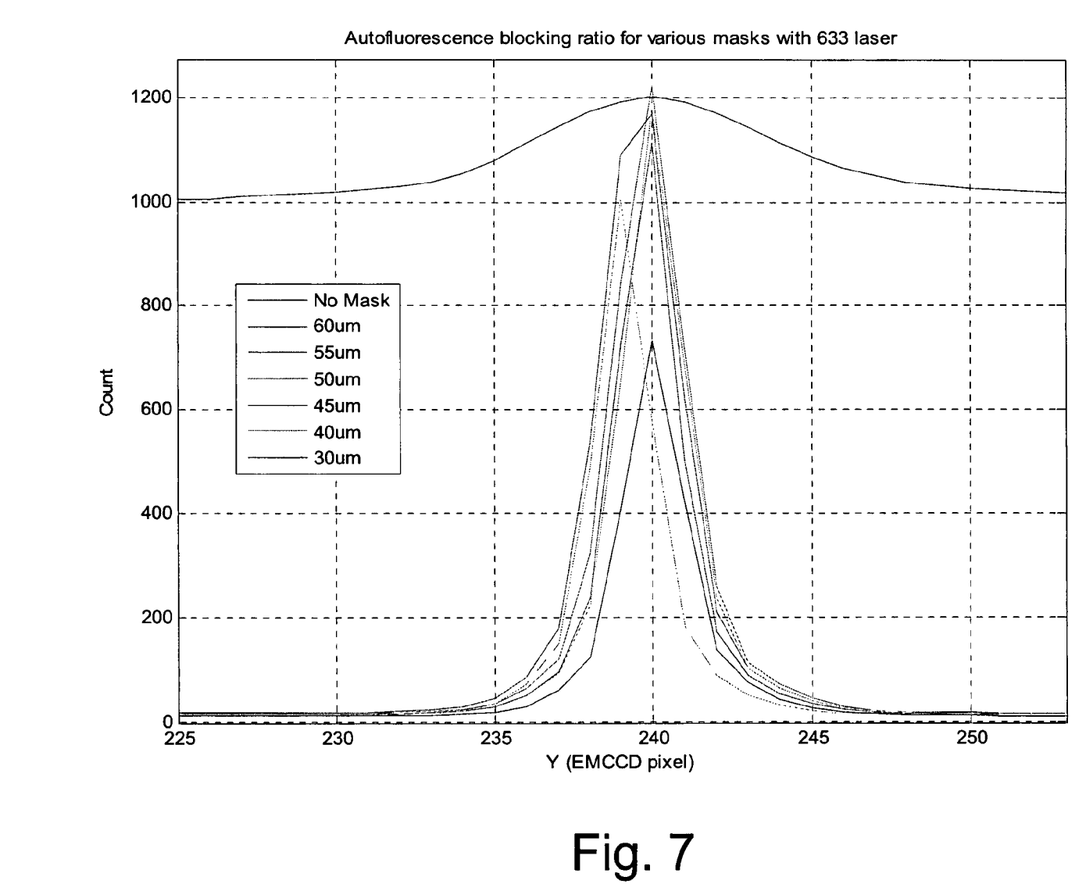
FIG. 7 is a comparative plot of autofluorescence imaged at a discrete detector location in the absence of a confocal mask, and in the presence of confocal slits of decreasing cross sectional dimensions.

FIG. 6 provides an illustration of the effects of out of focus autofluorescence as well as the benefits of a confocal mask in reducing such autofluorescence. In particular, FIG. 6 shows a plot of autofluorescence levels as a function of the location of the image of the autofluorescence on an EMCCD detector, from a substrate that was illuminated with four illumination lines at 488 nm. As shown, the upper plot 602 corresponds to autofluorescence image from 4 illumination lines, but in the absence of a confocal mask filtering the out of focus components. The 4 peaks (604-610) correspond to the elevated autofluorescence at the illumination lines on the substrate while the baseline corresponds to the overall global autofluorescence across the remainder of the substrate. By contrast, inclusion of a confocal mask provides a substantial reduction in the amount of the out of focus autofluorescence from the system. In particular, the lower plot 612, reflects the confocally filtered traces through a number of different slit sizes, where each aggregate peak (614-648) corresponds to the position of the slits in the confocal masks used. As can be seen, peaks 628-634 correspond to the location of the illumination lines, and as such have a higher amount of in focus autofluorescence. The remaining peaks also represent autofluorescence that is in the focal plane and thus not filtered by the confocal mask. FIG. 7 shows an expanded view of the various plots with illumination at 633 nm, with the upper plot reflecting an unfiltered level of autofluorescence imaged at a given position on the detector, while the lower plots reflect the autofluorescence at the same position but filtered using confocal masks having slit sizes of 60 nm, 55 nm, 50 nm, 45 nm, 40 nm, and 30 nm. The decreasing size of the autofluorescence peak is correlated to the reduction in the dimensions of the slit in the confocal mask used.

Notwithstanding this in focus component, it can be easily seen that the provision of the confocal mask provides a significant reduction in the overall autofluorescence that is detected (as indicated by the area under each of the two plots). As noted, the confocal mask used in the example shown in FIG. 6 employed confocal slits for a linear illumination profile. It will be appreciated that alternative mask configurations may be employed as well, such as the use of arrayed pin holes in the confocal mask, in order to provide arrayed spot or targeted illumination as discussed elsewhere herein.

Other additional approaches to reduction of generated autofluorescence include spectral filtering of autofluorescence noise, through the incorporation of appropriate filters within the optical train, and particularly the collection aspects of the optical train. It has been observed that a substantial amount of autofluorescence signal in a typical illumination profile, e.g., in a wavelength range of from about 720 nm to about 1000 nm, falls within spectral ranges that do not overlap with desired detection ranges, e.g., from about 500 nm to about 720 nm. As such, elimination of at least a portion of autofluorescence noise may be accomplished by incorporating optical filters that block light outside of the desired range, e.g., long or short pass filters that block light of a wavelength greater than about 720 nm or less than about 500 nm. Such filters are generally made to order from optical component suppliers, including, e.g., Semrock, Inc., Rochester N.Y., Barr Associates, Inc., Westford, Mass., Chroma Technology Corp., Rockingham Vt.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method of monitoring fluorescent signals from a source of fluorescent signals, comprising:
   providing a fluorescent signal detection system that comprises:
   a substrate comprising a plurality of discrete fluorescent signal sources;
   a source of excitation illumination;
   a fluorescent signal detector;
   an optical train for directing excitation illumination from the source of excitation illumination to the substrate, and for directing fluorescent signals from the substrate to the fluorescent signal detector; and,
   photobleaching at least one optical component in the optical train, so as to reduce a level of autofluorescence produced by the at least one optical component in response to passing excitation illumination therethrough.

2. A method of monitoring fluorescent signals from a source of fluorescent signals, comprising:
   providing an excitation illumination source, a substrate having at least a first fluorescent signal source disposed thereon, and an optical train comprising optical components and positioned to direct excitation illumination from the illumination source to the at least first fluorescent signal source, and for transmitting fluorescent signals from the at least first fluorescent signal source to a detector;
   photobleaching at least one optical componente of the optical train to reduce an amount of autofluorescence produced by the at least one optical component in response to the excitation illumination;
   directing excitation illumination through the at least one optical component and at the at least first fluorescent signal source; and,
   detecting fluorescent signals from the at least first fluorescent signal source.

3. The method of claim 2, wherein the fluorescent signals are confocally filtered prior to being detected.

4. The method of claim 1 or 2, wherein photobleaching comprises exposing the at least one optical component to illumination that is greater in intensity or power and duration relative to the excitation illumination directed to the fluorescent signal sources.

5. The method of claim 4, wherein the intensity or the power and duration of the illumination is at least two-fold greater than the excitation illumination.

6. The method of claim 4, wherein the intensity or the power and duration of the illumination is more than ten-fold greater than the excitation illumination.

7. The method of claim 1 or 2, wherein photobleaching comprises exposing the at least one optical component to illumination produced by a 20 mW laser at 488 nM for at least 20 hours.

8. The method of claim 7, wherein photobleaching further comprises exposing the at least one optical component to illumination produced by a 7.5 mW laser at 488 nM for no more than 1000 minutes, followed by exposing the at least one optical component to illumination produced by a 162 mW laser at 488 nM for 1000 to 4600 minutes.

* * * * *